(12) United States Patent
Verzini et al.

(10) Patent No.: US 9,290,428 B2
(45) Date of Patent: Mar. 22, 2016

(54) PROCESS FOR THE PREPARATION OF DERIVATIVES OF 1-(2-FLUORO[1,1'-BIPHENYL]-4-YL)-CYCLOPROPANECARBOXYLIC ACID

(71) Applicant: CHIESI FARMACEUTICI S.p.A, Parma (IT)

(72) Inventors: Massimo Verzini, Bresso (IT); Livius Cotarca, Bresso (IT); Alberto Guidi, Bresso (IT); Alfonso Melloni, Bresso (IT); Paolo Maragni, Bresso (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 14/311,630

(22) Filed: Jun. 23, 2014

(65) Prior Publication Data
US 2014/0378696 A1    Dec. 25, 2014

(30) Foreign Application Priority Data

Jun. 24, 2013 (EP) .................................. 13173368

(51) Int. Cl.
| | |
|---|---|
| C07C 51/09 | (2006.01) |
| C07C 51/08 | (2006.01) |
| C07C 67/343 | (2006.01) |
| C07C 253/30 | (2006.01) |
| C07C 67/22 | (2006.01) |

(52) U.S. Cl.
CPC ............... *C07C 51/09* (2013.01); *C07C 51/08* (2013.01); *C07C 67/343* (2013.01); *C07C 253/30* (2013.01); *C07C 2101/02* (2013.01)

(58) Field of Classification Search
CPC .. C07C 2101/02; C07C 51/08; C07C 67/343; C07C 253/30; C07C 51/09; C07C 255/46; C07C 69/753; C07C 61/40
See application file for complete search history.

(56) References Cited

U.S. PATENT DOCUMENTS

2011/0039934 A1* 2/2011 Pivetti et al. ................. 514/570

FOREIGN PATENT DOCUMENTS

| WO | 2009/149797 | 12/2009 |
| WO | WO 2014/206897 A2 * | 12/2014 |

OTHER PUBLICATIONS

Schiefer et al. "Inhibition of Amyloidogenesis by Nonsteroidal Anti-inflammatory Drugs and Their Hybrid Nitrates" J. Med. Chem. 2011, 54, 2293-2306.*

Arava et al. "Efficient cyclopropanation of active methylene compounds. A serendipitous discovery" Tetrahedron Lett. 2005, 46, 7247-7248.*
Carlson et al. "Hydroxyalkylation with Cyclic Alkylene Esters. I. Synthesis of Hydroxyethylapocupreine" J. Am. Chem. Soc. 1947, 69, 1952-1956.*
Scripps Research Institute "Rules of Thumb: Helpful Numerical Guidelines for Synthetic Organic Experiments" Sep. 8, 2004 [online] [retrieved Jul. 10, 2015] Retrieved from <http://www.scripps.edu/shenvi/Education_files/rules%20of%20thumb%20handout.pdf>.*
European Search Report in Application No. 13173368.5 issued Nov. 20, 2013.
Arava et al. Tetrahedron Letters, vol. 46 , pp. 7247-7248 (2005).

* cited by examiner

*Primary Examiner* — Joseph Kosack
*Assistant Examiner* — Amanda L Aguirre
(74) *Attorney, Agent, or Firm* — Oblon, McClelland, Maier & Neustadt, L.L.P.

(57) ABSTRACT

The present invention relates to a process for the preparation of a compound of formula (I) or a pharmaceutically acceptable salt thereof:

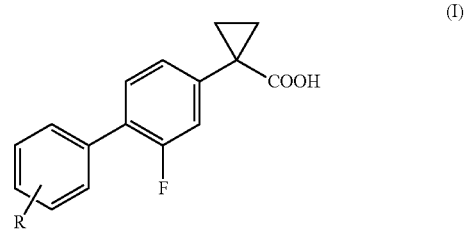

wherein R represents one or more groups independently selected from fluorine, chlorine, bromine, and iodine,
said process comprising the cyclopropanation of a compound of formula (II) with ethylene carbonate or ethylene sulfate:

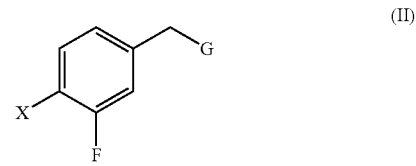

wherein X is chlorine, bromine, iodine or a triflate group ($CF_3SO_3$) or a group

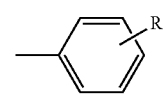

wherein R is as defined above and G is —CN or —$COOR_2$ wherein $R_2$ is a $C_1$-$C_4$ straight or branched alkyl chain.

20 Claims, No Drawings

PROCESS FOR THE PREPARATION OF DERIVATIVES OF 1-(2-FLUORO[1,1'-BIPHENYL]-4-YL)-CYCLOPROPANECARBOXYLIC ACID

CROSS REFERENCES TO RELATED APPLICATIONS

This application claims priority to European Patent Application No. 13173368.5, filed on Jun. 24, 2013.

The present invention relates to a process for the preparation of derivatives of 1-(2-fluoro[1,1'-biphenyl]-4-yl)-cyclopropanecarboxylic acid, in particular 1-(3',4'-dichloro-2-fluoro[1,1'-biphenyl]-4-yl)-cyclopropanecarboxylic acid, or pharmaceutically acceptable salts thereof.

The compounds of the following formula (I) are known to be useful in the prevention and treatment of neurodegenerative diseases, in particular Alzheimer's disease (WO 2004/074232):

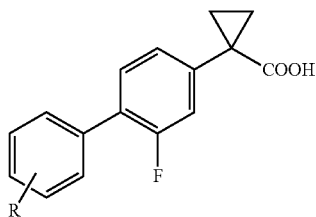

Different process have been developed for the preparation of said compounds.

In WO 2004/074232, the key intermediate step of the preparation of said compounds is the Suzuki reaction between a suitable phenylboronic acid or an ester thereof with a 3,4-dihalo-phenylcyclopropanecarboxylic acid, preferably a 3-fluoro-4-halo-cyclopropanecarboxylic acid.

The intermediate 3-fluoro-4-halo-phenylcyclopropanecarboxylic acid is obtained by the reaction of 3-fluoro-4-halophenylacetonitrile with 1,2-dibromoethane to give the corresponding 3-fluoro-4-halo-phenylcyclopropanenitrile which is finally hydrolyzed to 3-fluoro-4-halo-phenylcyclopropanecarboxylic acid.

WO2009/149797 discloses a process for the preparation of said compounds wherein the cyclopropanation with 1,2-dibromoethane is postponed after the Suzuki coupling right before the hydrolysis final step.

WO 2011/015287 discloses a process for the preparation of said compounds wherein the Suzuki reaction is carried out between a suitable phenylboronic acid or an ester thereof with 3-fluoro-4-halo-phenylcyclopropanenitrile. The intermediate 3-fluoro-4-halo-phenyl cyclopropanenitrile is obtained by the reaction of 3-fluoro-4-halophenylacetonitrile with 1,2-dibromoethane.

In the above reported processes the cyclopropanation reaction involves the use of 1,2-dibromo ethane to which toxicological concerns might be associated.

It is therefore advisable to avoid the use of 1,2-dibromo ethane in the production process of the compounds of formula (I).

The present invention provides a process for preparing the compounds of formula (I) wherein a safer reagent, such as ethylene carbonate or ethylene sulfate, is used in the cyclopropanation step.

Ethylene carbonate is known to give cyclopropanation on the reactive methylene group of arylacetonitriles (Arava et al. Tetrahedron Letters 46 (2005) 7247-7248). The yield of the reaction is lower than 55% and the obtained compounds are unstable in the reaction mixture. Therefore the end products have a high content of impurities.

It has now been found that the cyclopropanation reaction with ethylene carbonate can be applied to the compounds of Formula (II) as reported below, under specific conditions to obtain the corresponding cyclopropane derivative in a high yield.

Furthermore it has been found that high yields can also be obtained using ethylene sulfate as reagent.

The present invention provides a process for the preparation of a compound of formula (I) or a pharmaceutically acceptable salt thereof:

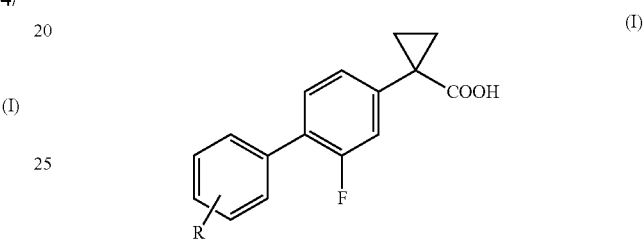

wherein R represents one or more groups independently selected from fluorine, chlorine, bromine, and iodine, preferably chlorine, said process comprising the following steps:

i) reacting a compound of formula (II):

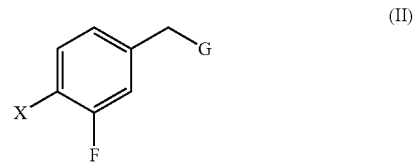

wherein X is chlorine, bromine, iodine or a triflate group ($CF_3SO_3$) or a group

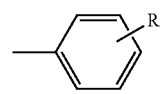

wherein R is as defined above and G is —CN or —$COOR_2$ wherein $R_2$ is a $C_1$-$C_4$ straight or branched alkyl chain, with a compound of formula (III):

wherein Y is CO or $SO_2$ in the presence of a base,
with the proviso that:
when Y is CO the reaction is carried out at a temperature ranging from 120° C. to 180° C. and the molar ratio between the compound of formula (II) and the compound of formula (III) is from 1:10 to 1:30.
when G is —COOR$_2$ then Y is SO$_2$;
to obtain a compound of formula (IV):

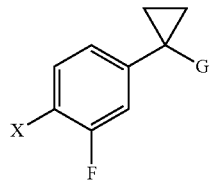

(IV)

wherein X and G are as defined above;
ii) coupling the compound of formula (IV) wherein X is chlorine, bromine, iodine or a triflate group (CF$_3$SO$_3$)
with a compound of formula (V)

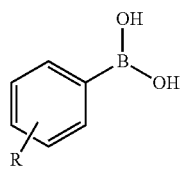

(V)

wherein R is as defined above,
to obtain a compound of formula (IV) wherein X is

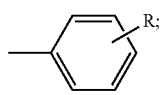

iii) hydrolyzing the compound of formula (IV) wherein X is

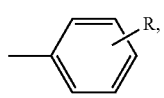

obtained in step i) or ii), to give a compound of formula (I);
iv) optionally transforming the compound of formula (I) obtained in the previous step into a pharmaceutically acceptable salt thereof.

The term "pharmaceutically acceptable salts" refers to salts obtained by reacting the main compound, in acid form, with an inorganic or organic base to form a salt approved for human use, e.g., sodium, potassium, calcium, magnesium, and ammonium salts.

Straight chain or branched C$_1$-C$_4$ alkyl may be methyl, ethyl, n-propyl, isopropyl, n-butyl, isobutyl, sec-butyl, tert-butyl, preferably ethyl.

X is preferably bromine or

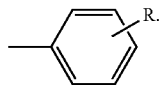

The present process is preferably used for the preparation of 1-(3',4'-dichloro-2-fluoro[1,1'-biphenyl]-4-yl)-cyclopropanecarboxylic acid of formula:

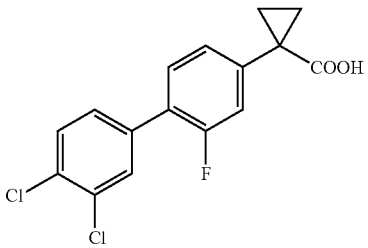 [SMILES: O=C(O)C1(c2ccc(-c3ccc(Cl)c(Cl)c3)c(F)c2)CC1]

or a pharmaceutically salt thereof.

The reaction steps i)-iii) can be carried out according the preferred conditions reported herebelow.

Step i)

The base used in step i) is preferably selected from the group consisting of sodium, potassium or lithium tertbutylate, potassium carbonate, sodium hydride, lithium bis(trimethylsilyl)amide (LiHMDS), lithium diisopropylamide (LDA).

When Y is CO, i.e. the compound of formula (III) is ethylene carbonate, the reaction of step i) may be carried out either without a solvent or in an aprotic organic solvent such as dimethoxyethane (DME), dimethylformamide (DMF), dimethylsulfoxide (DMSO), tetrahydrofuran (THF), toluene, N-methyl-2-pyrrolidone (NMP), toluene, at a temperature ranging from 120° C. to 180° C., preferably from 130° to 160°. The temperature may depend on the kind of base used in the reaction, for example when the base is sodium carbonate the reaction is carried out preferably at a temperature ranging from 160° C. to 180° C. When the base is lithium tertbutylate the reaction is carried out preferably at a temperature ranging from 120° C. to 140° C., most preferably at 130° C.

Furthermore very high yields are obtained when the reaction is carried out with a large excess of the reagent of formula (III), i.e. ethylene carbonate. The molar ratio between the compound of formula (II) and ethylene carbonate is from 1:10 to 1:30, preferably from 1:20 to 1:30.

The stability of the reaction product of formula (IV) in the reaction mixture, and therefore the yield of the reaction, increases when a catalyst is added to the reaction mixture. The catalyst is a compound able to complex alkaline metal cations which is preferably selected from the group consisting of polyethylene glycols (PEG), phosphonium salts, crown ethers.

Preferably the catalyst is selected from the group consisting of PEG-200, PEG 6000.

Preferably the compound of formula (II) and the catalyst are present in a molar ratio ranging from 1:0.02 to 1:2.

When Y is SO$_2$, i.e. the compound of formula (III) is ethylene sulfate, the reaction of step i) may be carried out in an aprotic organic solvent such as dimethoxyethane (DME), dimethylformamide (DMF), dimethylsulfoxide (DMSO), tetrahydrofuran (THF), N-methyl-2-pyrrolidone (NMP), toluene, at a temperature ranging from −20° C. to reflux, preferably from −20° C. to 20° C.

Preferably the molar ratio between the compound of formula (II) and ethylene sulfate is from 1:1 to 1:1.5 and most preferably from 1:1.1 to 1:1.2.

Step ii)

Step ii) may be carried out according known methods such as the procedure described in WO2011/015287 (p. 7 line 24 to p. 9 line 20 and Example 4).

Step iii)

Step iii) may be carried out according known methods such as the procedure described in WO2011/015287 (p. 9 line 21 to p. 10 line 4 and Example 5) or in WO2009/149797 (p. 10 line 13 to line 27 and Example 5).

The compounds of formula (II) wherein G is CN and X is chlorine, bromine, iodine or a triflate group ($CF_3SO_3$) can be prepared according to known methods from commercial products such as the procedure described in WO2011/015287 (p. 11 line 1 to p. 12 line 15 and Examples 1 and 2).

The compounds of formula (II) wherein G is CN and X is

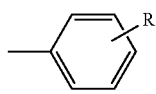

can be prepared according to known methods, such as the procedure described in WO2009/149797 (p. 6 line 14 to p. 9 line 24 and Examples 1-3), from commercial products.

The compounds of formula (II) wherein G is $COOR_2$ and X is as defined above are commercial products or they can be prepared from the corresponding compound of formula (II) wherein G is CN according to known methods such as the Pinner reaction (EP0253501A2; JOC 2010, 75, 945-947).

The compounds of formula (III) are commercially available.

The boronic acid of formula (V) or the corresponding boronates are either commercially available or can be prepared from the corresponding halide according to methods known in literature.

The compounds of formula (I) obtained by the processes of the invention may be used in the preparation of pharmaceutical compositions for the treatment and/or the prevention of neurodegenerative diseases such as Alzheimer's disease.

Said pharmaceutical compositions, preferably for the oral use, comprise at least one compound of formula (I) in admixture with pharmaceutically acceptable excipients and/or carriers, for example those described in Remington's Pharmaceutical Sciences Handbook, XVII Ed., Mack Pub., N.Y., U.S.A.

The invention is illustrated in greater detail in the following Examples.

EXAMPLE 1

Cyclopropanation of 4-bromo-3-fluorophenylacetonitrile (II) with ethylene carbonate (III) to give 4-bromo-3-fluorophenyl-cyclopropanenitrile (IV)

Ethylene carbonate (370.2 g, 4.204 mol, 30.0 eq.) was loaded in a 500 ml reactor at room temperature and heated to an internal temperature of 40° C. till all the solid melted. Then 1.4 g of PEG-200 (0.007 mol, 0.05 eq.) and 30.0 g of 4-bromo-3-fluorophenylacetonitrile (0.140 mol, 1.0 eq.) were charged in the reactor. Potassium tert-butoxide (31.4 g, 0.280 mol, 2.0 eq.) was added portion-wise, under stirring, to the resulting clear colorless solution. The internal temperature rose to 60° C. Then, the mixture was heated to 130° C. and kept under stirring for 8 hours. The mixture was cooled to 40° C. and then 105 g of toluene and 240 g of deionised water were added. The mixture was kept under stirring for 15 minutes at 40° C. and then stirring was stopped. After 15 minutes two layers were separated: a lower organic clear red phase and an upper aqueous colorless phase. The organic solution was reloaded into the reactor and heated to an internal temperature of 40° C. 240 g of deionised water were added. The mixture was kept under stirring for 15 minutes at 40° C. and then stirring was stopped. After 30 minutes the yellowish opalescent aqueous layer (lower) was discarded, and the organic phase was washed again two times with 240 g of deionised water. After 30 minutes, the yellowish opalescent aqueous layer was discarded. The organic solution was warmed to 80° C. and the volatile solvents were removed under reduced pressure until 36 ml as the final volume. A solution 9.6 g of isopropyl alcohol was added. The solution was cooled from 80° C. to 50° C. in 30 minutes and a small amount of seed was added. The crystallization mixture was cooled from 50° C. to 0° C. in 60 minutes. The suspension was stirred for at least 60 minutes then filtered washing three times with 9.0 g of a toluene/isopropyl alcohol mixture (1/1.25 w/w). The wet product was dried under vacuum at 40° C. for 15-18 hours. 22.7 g of a pale yellow solid were obtained (purity=99.94%; molar yield=68%).

EXAMPLE 2

Cyclopropanation of 4-bromo-3-fluorophenylacetonitrile (II) with ethylene sulfate (III) to give 4-bromo-3-fluorophenyl-cyclopropanenitrile (IV)

24 ml of lithium bis(trimethylsilyl)amide (1M in THF, 24 mmol, 2.2 eq.) were loaded at T=−20° C. in a 50 ml dried reactor under nitrogen. 2.34 g of 4-bromo-3-fluorophenylacetonitrile (10.92 mmol, 1.0 eq.), dissolved in 5 ml of dry THF, and 1.49 g of ethylene sulfate (12.0 mmol, 1.1 eq.), dissolved in 5 ml of dry THF, were added in the reactor. The mixture was kept under stirring at T=−20° C. for 4 h and then heated to 20° C. The reaction was quenched by adding $NH_4Cl$ (saturated solution) and extracted with toluene. The organic layer was concentrated to dryness at reduced pressure to yield 3.01 g of crude product (assay=69.4%; molar yield=79.7%).

EXAMPLE 3

Preparation of ethyl 3-fluoro-4-bromo-phenylacetate from 3-fluoro-4-bromo-phenylacetonitrile 2.5 g of 3-fluoro-4-bromo-phenylacetonitrile, 4.7 g. of ethyl alcohol and 4.7 g of sulfuric acid were loaded at room temperature in an reactor. The mixture was heated to 100° C. and stirred for 5 hours. When the conversion was completed, the mixture was cooled to room temperature, water and ethyl acetate were added and the aqueous phase was re-extracted with fresh ethyl acetate. The organic phase was washed with a sodium bicarbonate/water solution, then with water until pH=7. The organic phase was concentrated to yield 2.6 g, of crude product.

EXAMPLE 4

Cyclopropanation of ethyl 4-bromo-3-fluorophenylacetate (II) with ethylene sulfate (III) to give the ethyl ester of 4-bromo-3-fluorophenyl-cyclopropane carboxylic acid. (IV)

6.6 ml of lithium diisopropylamide (2M in THF/heptane/ethylbenzene, 13.2 mmol, 2.2 eq.) were loaded into a 50 ml dried reactor at T=−20° C. under nitrogen. 1.71 g of 3-fluoro-4-bromophenylacetate (6.0 mmol, 1.0 equiv.), dissolved in 8 ml of dry THF, and 0.82 g of ethylene sulfate (6.6 mmol, 1.1 equiv.), dissolved in 8 ml of dry THF, were added dropwise in 10 minutes. The mixture was kept under stirring at T=−20° C. for 3 h then heated to 20° C. and maintained under reflux for 5 h. The mixture was cooled to room temperature. The reaction was quenched by adding $NH_4Cl$ (saturated solution) and extracted with toluene. The organic layer was concentrated to dryness at reduced pressure to yield 1.15 g of crude product (purity=72.4%).

EXAMPLE 5

Cyclopropanation of 2-(3',4'-dichloro-2-fluoro[1,1'-biphenyl]-4-yl)-acetonitrile (II) with ethylene carbonate (III) to give the 1-(3',4'-dichloro-2-fluoro[1,1'-biphenyl]-4-yl)-cyclopropanenitrile (IV)

Ethylene carbonate (7.6 g, 86.3 mmol, 30.0 eq.) was loaded in a 25 ml flask at room temperature and heated to an internal temperature of 45° C. till all the solid melted. Then 32 mg of PEG-200 (0.16 mmol, 0.05 eq.) and 800 mg of 143%4% dichloro-2-fluoro[1,1'-biphenyl]-4-yl)-acetonitrile (2.88 mmol, 1.0 eq.) were loaded in the reactor. Potassium tert-butoxide (646 mg, 5.75 mmol, 2.0 eq.) was added portion-wise, under stirring, to give a clear brown solution. Then, the mixture was heated to 130° C. and kept under stirring for 7 hours. The mixture was cooled to 40° C. and then 10 g of toluene and 10 g of deionised water were added. The two layers were separated and the aqueous phase was extracted with toluene. The organic phases were collected and washed with deionised water. The aqueous phase was discarded and the organic layer was concentrated to dryness at reduced pressure to yield 1.0 g of crude product (purity=80.0%).

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for preparing a compound of formula (I) or a pharmaceutically acceptable salt thereof:

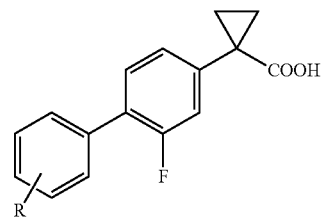

(I)

wherein R represents one or more substituents independently selected from the group consisting of fluorine, chlorine, bromine, and iodine,
said process comprising:
(i) reacting a compound of formula (II):

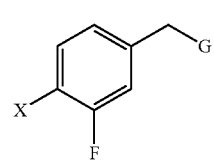

(II)

wherein X is chlorine, bromine, iodine or a triflate group ($CF_3SO_3$) or a group

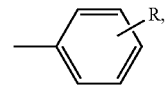

wherein R is as defined above, and G is —CN or —$COOR_2$, wherein $R_2$ is a $C_1$-$C_4$ straight or branched alkyl chain,
with a compound of formula (III):

(III)

wherein Y is CO or $SO_2$ in the presence of a base,
with the provisos that:
(a) when Y is CO, then said reacting is carried out at a temperature of 120° C. to 180° C. and the molar ratio of said compound of formula (II) to said compound of formula (III) is 1:10 to 1:30 and said reacting is carried out in the presence of a compound able to complex an alkaline metal cation, said compound being selected from the group consisting of a polyethylene glycol, a phosphonium salt, and a crown ether; and
(b) when G is —COOR$_2$, then Y is SO$_2$;
to obtain a compound of formula (IV):

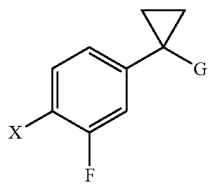

wherein X and G are as defined above;
(ii) when X is chlorine, bromine, iodine or a triflate group (CF$_3$SO$_3$), coupling said compound of formula (IV) with a compound of formula (V):

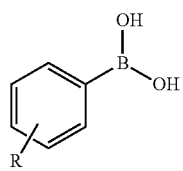

wherein R is as defined above,
to obtain a compound of formula (IV) wherein X is

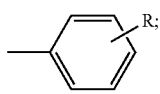

(iii) hydrolyzing said compound of formula (IV) wherein X is

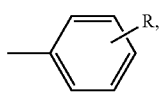

obtained in (i) or (ii), to obtain said compound of formula (I); and
(iv) optionally transforming said compound of formula (I) into a pharmaceutically acceptable salt thereof.

2. A process according to claim 1, wherein G is —CN or —COOEt.

3. A process according to claim 1, wherein, in said compound of formula (II), X is bromine.

4. A process according to claim 1, wherein, in said compound of formula (II), X is

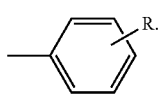

5. A process according to claim 1, wherein said compound of formula (I) is 1-(3',4'-dichloro-2-fluoro[1,1'-biphenyl]-4-yl)-cyclopropanecarboxylic acid of

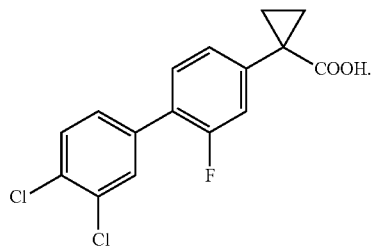 [SMILES: O=C(O)C1(c2ccc(-c3ccc(Cl)c(Cl)c3)c(F)c2)CC1]

6. A process according to claim 1, wherein, in (i), said base is selected from the group consisting of sodium tertbutylate, potassium tertbutylate, lithium tertbutylate, potassium carbonate, sodium hydride, lithium bis(trimethylsilyl)amide (LiHMDS); and lithium diisopropylamide (LDA).

7. A process according to claim 1, wherein Y is CO.

8. A process according to claim 7, wherein, in (i), the reaction is carried out at a temperature of 130° C. to 160° C.

9. A process according to claim 7, wherein, in (i), the molar ratio of said compound of formula (II) to said compound of formula (III) is 1:20 to 1:30.

10. A process according to claim 8, wherein, in (i), the molar ratio of said compound of formula (II) to said compound of formula (III) is 1:20 to 1:30.

11. A process according to claim 1, wherein said compound able to complex an alkaline metal cation is selected from the group consisting of PEG-200 and PEG-6000.

12. A process according to claim 1, wherein said compound of formula (II) and said compound able to complex an alkaline metal cation are present in a molar ratio of 1:0.02 to 1:2.

13. A process according to claim 1, wherein Y is SO$_2$.

14. A process according to claim 13, wherein, in (i), the reaction is carried out at a temperature of from −20° C. to reflux temperature.

15. A process according to claim 13, wherein, in (i) the molar ratio of said compound of formula (II) to said compound of formula (III) is from 1:1 to 1:1.2.

16. A process for preparing a compound of formula (IV) or a pharmaceutically acceptable salt thereof:

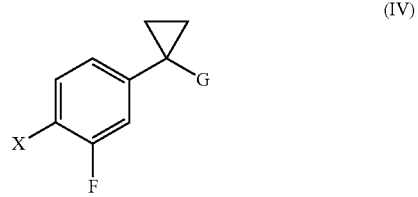

wherein X is chlorine, bromine, iodine or a triflate group (CF$_3$SO$_3$) or a group

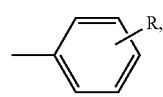

wherein R represents one or more substituents independently selected from the group consisting of fluorine, chlorine, bromine, and iodine, and G is —CN or —COOR$_2$, wherein R$_2$ is a C$_1$-C$_4$ straight or branched alkyl chain
said process comprising:
(i) reacting a compound of formula (II):

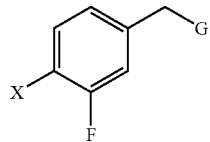
(II)

with a compound of formula (III):

(III)

wherein Y is CO or SO$_2$ in the presence of a base,
with the provisos that:
(a) when Y is CO, then said reacting is carried out at a temperature of 120° C. to 180° C. and the molar ratio of said compound of formula (II) to said compound of formula (III) is 1:10 to 1:30 and said reacting is carried out in the presence of a compound able to complex an alkaline metal cation, said compound being selected from the group consisting of a polyethylene glycol, a phosphonium salt, and a crown ether; and
(b) when G is —COOR$_2$, then Y is SO$_2$;
to obtain said compound of formula (IV).

17. A process according to claim 16, wherein G is —CN or —COOEt.

18. A process according to claim 16, wherein, in said compound of formula (II), X is bromine.

19. A process according to claim 16, wherein, in said compound of formula (II), X is

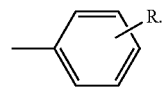

20. A process according to claim 16, wherein, in (i), said base is selected from the group consisting of sodium tertbutylate, potassium tertbutylate, lithium tertbutylate, potassium carbonate, sodium hydride, lithium bis(trimethylsilyl)amide (LiHMDS); and lithium diisopropylamide (LDA).

* * * * *